US00PP13042P2

(12) United States Plant Patent
Drewlow

(10) Patent No.: US PP13,042 P2
(45) Date of Patent: Oct. 1, 2002

(54) NEW GUINEA IMPATIENS PLANT NAMED 'LASTING IMPRESSIONS RED'

(75) Inventor: Lyndon W. Drewlow, Lompoc, CA (US)

(73) Assignee: Oglevee Ltd., Connellsville, PA (US)

( * ) Notice: Subject to any disclaimer, the term of this patent is extended or adjusted under 35 U.S.C. 154(b) by 0 days.

(21) Appl. No.: 09/876,933

(22) Filed: Jun. 11, 2001

(51) Int. Cl.[7] ..... A01H 5/00
(52) U.S. Cl. ..... Plt./318

(58) Field of Search ..... Plt./318

*Primary Examiner*—Bruce R. Campell
*Assistant Examiner*—Annette H. Para
(74) *Attorney, Agent, or Firm*—C. A. Whealy

(57) ABSTRACT

A new and distinct cultivar of New Guinea Impatiens plant named 'Lasting Impressions Red', characterized by its very large and rounded dark red-colored flowers; freely flowering habit with flowers positioned above or beyond the foliage; mounded to semi-upright plant habit; freely branching growth habit; dark green-colored leaves; and tolerance to full sun conditions and high and low temperatures.

1 Drawing Sheet

BOTANICAL CLASSIFICATION

*Impatiens hawkeri* cultivar Lasting Impressions Red.

BACKGROUND OF THE INVENTION

The present Invention relates to a new and distinct cultivar of New Guinea Impatiens plant, botanically known as *Impatiens hawkeri*, and hereinafter referred to by the cultivar name Lasting Impressions Red.

The new Impatiens is a product of a planned breeding program conducted by the Inventor in Ashtabula, Ohio. The objective of the breeding program is to develop new intermediate-sized New Guinea Impatiens cultivars with numerous large rounded flowers and interesting flower and foliage colors.

The new Impatiens originated from a cross made by the Inventor during the winter of 1996/1997 of a proprietary *Impatiens hawkeri* seedling selection designated as code number 95-306-9, not patented, as the female, or seed parent, with a proprietary *Impatiens hawkeri* seedling selection designated as code number 96-1089-60, not patented, as the male, or pollen parent. The cultivar Lasting Impressions Red was discovered and selected by the Inventor as a flowering plant within the progeny of the stated cross in controlled environment in Ashtabula, Ohio.

Asexual reproduction of the new cultivar by terminal cuttings taken in Ashtabula, Ohio, since May, 1997, has shown that the unique features of this new Impatiens are stable and reproduced true to type in successive generations. Plants of the new Impatiens differ from plants of the parent selections primarily in plant growth habit, flower shape and color.

SUMMARY OF THE INVENTION

The following traits have been repeatedly observed and are determined to be the unique characteristics of 'Lasting Impressions Red'. These characteristics in combination distinguish 'Lasting Impressions Red' as a new and distinct Impatiens cultivar:

1. Very large, rounded, dark red-colored flowers.
2. Freely flowering habit with flowers positioned above or beyond the foliage.

3. Mounded to semi-upright plant habit.
4. Freely branching growth habit.
5. Dark green-colored leaves.
6. Tolerant to full sun conditions and high and low temperatures.

Plants of the new Impatiens can be compared to plants of the cultivar Blazon, disclosed in U.S. Plant Pat. No. 7,793. In side-by-side comparisons conducted by the Inventor in Lompoc, Calif., plants of the new Impatiens differ from plants of the cultivar Blazon, in the following characteristics:

1. Plants of the new Impatiens are shorter, more mounded and not as upright as plants of the cultivar Blazon.
2. Leaves of plants of the new Impatiens are solid dark green in color whereas leaves of plants of the cultivar Blazon are green and yellow variegated.
3. Plants of the new Impatiens have larger flowers than plants of the cultivar Blazon.

Plants of the new Impatiens can also be compared to plants of the cultivar BFP-523 Deep Red, disclosed in U.S. Plant Pat. No. 9,521. In side-by-side comparisons conducted by the Inventor in Lompoc, Calif., plants of the new Impatiens differ from plants of the cultivar BFP-523 Deep Red, in the following characteristics:

1. Plants of the new Impatiens are shorter, more mounded and not as upright as plants of the cultivar BFP-523 Deep Red.
2. Plants of the new Impatiens have larger flowers than plants of the cultivar BFP-523 Deep Red.
3. Flower color of the new Impatiens is slightly darker red than flower color of the cultivar BFP-523 Deep Red.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens.

The photograph comprises a top perspective view of a typical flowering plant of 'Lasting Impressions Red' grown during the winter in Lompoc, Calif., in a 15-cm container for about 8 to 10 weeks after planting a rooted cutting.

DETAILED BOTANICAL DESCRIPTION

The cultivar Lasting Impressions Red has not been observed under all possible environmental conditions. The phenotype may vary somewhat with variations in environment such as temperature, light intensity, daylength, water status and/or fertilizer type or rate, without, however, any variance in genotype. The following observations and measurements describe plants grown in Lompoc, Calif., during the winter, under commercial practice in a fiberglass-covered greenhouse. Plants used in the following description were grown in 15-cm containers for about 8 to 10 weeks after planting rooted cuttings. During the production period, day temperatures ranged from 21 to 24° C., night temperatures ranged from 16 to 18° C., and light levels ranged from 3,000 to 4,000 foot-candles.

In the following description, color references are made to The Royal Horticultural Society Colour Chart except where general terms of ordinary dictionary significance are used.

Botanical classification: *Impatiens hawkeri* cultivar Lasting Impressions Red.

Commercial classification: New Guinea Impatiens cultivar Lasting Impressions Red.

Parentage:

*Female parent.*—Proprietary *Impatiens hawkeri* seedling selection designated as code number 95-306-9, not patented.

*Male parent.*—Proprietary *Impatiens hawkeri* seedling selection designated as code number 96-1089-60, not patented.

Propagation:

*Type cutting.*—Terminal cuttings.

*Time to initiate roots.*—Summer: About 10 days at 21° C. Winter: About 12 days at 21° C.

*Time to produce a rooted cutting.*—Summer and winter: About 21 days at 21° C.

*Root description.*—Numerous, white, fine, fibrous and freely branching.

Plant description:

*General appearance.*—Mounded to semi-upright plant habit, intermediate in size.

*Growth and branching habit.*—Freely branching and densely foliated, typically more than 10 lateral branches per plant develop; pinching, that is, removal of the terminal apices, is typically not required. Vigorous growth habit.

*Crop time.*—To produce a finished flowering plant in a 15-cm container: About 8 to 10 weeks from a rooted cutting. To produce a finished flowering plant in a 25-cm container: About 10 to 12 weeks from a rooted cutting.

*Plant height.*—About 22.5 cm.

*Plant spread.*—About 37.5 cm.

*Lateral branch description.*—Length: About 10 to 20 cm. Diameter: About 8 to 12 mm. Internode length: About 3 to 4 cm. Texture: Smooth, glabrous. Color: 146B overlain with 59B.

*Foliage description.*—Arrangement: Alternate or in whorls of five. Length, mature leaves: About 13 cm. Width, mature leaves: About 5.5 cm. Shape: Lanceolate. Apex: Acuminate. Base: Acute. Margin: Serrulate with fine ciliation. Texture: Smooth, glabrous. Venation pattern: Pinnate. Color: Young foliage, upper surface: 146A. Young foliage, lower surface: 146B. Fully expanded foliage, upper surface: 147A. Fully expanded foliage, lower surface: 148A. Venation, both surfaces: 147A. Petiole: Length: About 1 cm. Diameter: About 4 mm. Texture: Smooth, glabrous. Color: 59B.

Flower description:

*Flower type and flowering habit.*—Single, large and rounded dark red flowers. Freely flowering, usually about two flowers per leaf axil and about 10 flowers and flower buds per lateral branch. Flowers positioned above and beyond the foliage and typically face upward or outward. Flowers flat when fully opened. Flowers last about two weeks on the plant depending on environmental conditions. Petals self-cleaning; gynoecium persistent. Flowers not fragrant. Flowering indeterminate and continuous.

*Flowering season.*—Year-round under greenhouse conditions. In the garden, flowering from spring until fall.

*Flower diameter.*—About 7 cm.

*Flower buds.*—Rate of opening: From flower bud to fully open flower, typically about 5 to 7 days depending on temperature. Length: About 1.8 cm. Diameter: About 1.2 cm. Shape: Ellipsoidal. Texture: Smooth, glabrous. Color, just before opening: 45A.

*Petals.*—Quantity: Single, five per flower, imbricate. Length: About 3.2 cm. Width: About 4.25 cm. Shape: Roughly cordate. Apex: Emarginate. Base: Rounded, obtuse. Margin: Entire. Texture: Smooth; satiny. Color: Upper surface, when opening and fully opened: 45A; with subsequent development, 46B. Lower surface, when opening and fully opened: 45C.

*Spur.*—Length: About 6 cm. Texture: Smooth, glabrous. Color: 59B, green towards apex.

*Peduncles.*—Length: About 6 cm. Strength: Strong, flexible. Aspect: About 45° from the stem. Color: 146C, slightly overlain with red, close to 59B.

*Reproductive organs.*—Androecium: Stamen number: Five fused at anthers, filaments free, hooded. Anther shape: Obovate. Anther length: About 7 mm. Anther color: 45A. Amount of pollen: Abundant. Pollen color: White. Gynoecium: Pistil number: One. Pistil length: About 6 mm. Stigma shape: Columnar, five-segmented. Stigma color: White with red tint. Style color: White. Ovary color: 146B.

*Seed development.*—Seed development has not been observed.

Disease tolerance: Plants of the new Impatiens have been observed to be tolerant to pathogens common to Impatiens, such as Botrytis.

Temperature and light tolerance: In Connellsville, Pa., plants of the new Impatiens have been observed to be tolerant to full sun conditions and high temperatures, 32 to 38° C., during the summer and continue to flower. In Lompoc, Calif., plants of the new Impatiens have been observed to be tolerant to low night temperatures, about 5 to 10° C., and to continue to flower.

It is claimed:

1. A new and distinct cultivar of New Guinea Impatiens plant named 'Lasting Impressions Red', as illustrated and described.

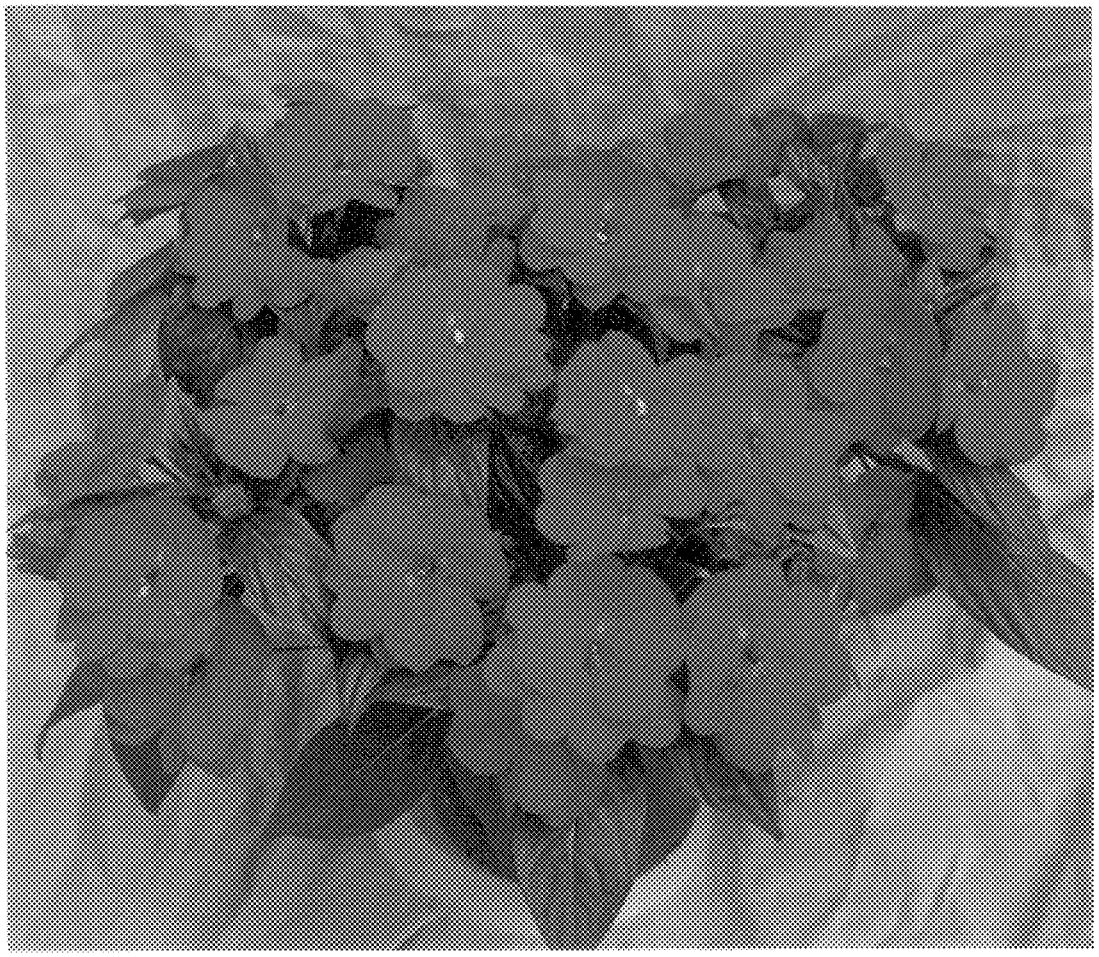

* * * * *